United States Patent
Kweon et al.

(10) Patent No.: US 10,695,459 B2
(45) Date of Patent: Jun. 30, 2020

(54) METHOD FOR PREPARING HIGH-FUNCTIONAL SUTURE YARN COATED WITH HYALURONATE AND HIGH-FUNCTIONAL SUTURE YARN PREPARED THEREFROM

(71) Applicant: JINWOO BIO CO., LTD., Seoul (KR)

(72) Inventors: Dong Keon Kweon, Yongin-si (KR); Seung Hyeon Park, Seoul (KR)

(73) Assignee: JINWOO BIO CO., LTD., Seoul (KR)

( * ) Notice: Subject to any disclaimer, the term of this patent is extended or adjusted under 35 U.S.C. 154(b) by 5 days.

(21) Appl. No.: 15/757,570

(22) PCT Filed: Sep. 1, 2016

(86) PCT No.: PCT/KR2016/009749
§ 371 (c)(1),
(2) Date: Mar. 5, 2018

(87) PCT Pub. No.: WO2017/039336
PCT Pub. Date: Mar. 9, 2017

(65) Prior Publication Data
US 2019/0015544 A1   Jan. 17, 2019

(30) Foreign Application Priority Data

Sep. 3, 2015 (KR) .................. 10-2015-0125087

(51) Int. Cl.
*A61L 17/14*  (2006.01)
*A61L 17/04*  (2006.01)
(Continued)

(52) U.S. Cl.
CPC ............ *A61L 17/145* (2013.01); *A61L 17/04* (2013.01); *A61L 17/10* (2013.01); *C08L 5/08* (2013.01)

(58) Field of Classification Search
CPC .................... A61L 17/45; A61F 2/00
(Continued)

(56) References Cited

U.S. PATENT DOCUMENTS

2005/0142163 A1 * 6/2005 Hunter .................. A61B 17/11
424/423
2010/0069957 A1   3/2010 Abuzaina et al.
(Continued)

FOREIGN PATENT DOCUMENTS

EP   1319415 A1   6/2003
JP   3463596 B2   8/2003
(Continued)

OTHER PUBLICATIONS

Drugbank, Hyaluronic Acid, 2020, Drugbank, pp. 1-11 (Year: 2020).*

(Continued)

*Primary Examiner* — Dah-Wei D. Yuan
*Assistant Examiner* — Andrew J Bowman
(74) *Attorney, Agent, or Firm* — Novick, Kim & Lee, PLLC; Jae Youn Kim

(57) ABSTRACT

Provided are a method of manufacturing a hyaluronate-coated high-functional suture and a high-functional suture manufactured thereby, and more particularly to a method of manufacturing a high-functional suture and a high-functional suture manufactured thereby, wherein a suture for internal and external surgery derived from a conventional chemical synthetic material is coated with a hyaluronate as a biocompatible material, thus improving biocompatibility, functionality and ease of use.

3 Claims, 4 Drawing Sheets

(51) Int. Cl.
*A61L 17/10* (2006.01)
*C08L 5/08* (2006.01)

(58) Field of Classification Search
USPC .......................................................... 424/490
See application file for complete search history.

(56) References Cited

U.S. PATENT DOCUMENTS

| | | | |
|---|---|---|---|
| 2010/0198257 | A1 | 8/2010 | Stopek et al. |
| 2014/0135833 | A1 | 5/2014 | Thomas et al. |
| 2014/0213966 | A1 | 7/2014 | Ostapoff et al. |
| 2016/0067208 | A1* | 3/2016 | Tabata ................... A61K 31/23 514/25 |

FOREIGN PATENT DOCUMENTS

| | | |
|---|---|---|
| JP | 2011-031034 A | 2/2011 |
| JP | 2011031034 A | 2/2011 |
| JP | 2012-501391 A | 1/2012 |
| JP | 2014-533992 A | 12/2014 |
| JP | 2018509212 A | 4/2018 |
| KR | 10-2012-0036226 A | 4/2012 |
| KR | 10-2012-0117609 A | 10/2012 |
| KR | 10-2015-0064454 A | 6/2015 |
| WO | WO0156626 * 8/2001 ............. A61L 17/08 |
| WO | 2013-055832 A1 | 4/2013 |
| WO | 2014-021954 A2 | 2/2014 |

OTHER PUBLICATIONS

Nguyen Ba, Technical Data Sheet Sodium Hyaluronate, 2020, Nguyen Ba Trading and Manufacturing Co. Ltd, pp. 1-2 (Year: 2020).*

Park et al., Guided bone regeneration by poly(lactic-co-glycolic acid) grafted hyaluronic acid bi-layer films for peridontal barrier applications, 2009, Acta Biomaterialia, pp. 3394-3403 (Year: 2009).*

Park et al., Guided bone regeneration by poly(lactic-co-glycolic acid) grafted hyaluronic acid bi-layer films for periodontal barrier applications, Acta Biomaterialia, Nov. 1, 2009, pp. 3394-3403, vol. 5, No. 9, Amsterdam.

* cited by examiner

METHOD FOR PREPARING HIGH-FUNCTIONAL SUTURE YARN COATED WITH HYALURONATE AND HIGH-FUNCTIONAL SUTURE YARN PREPARED THEREFROM

TECHNICAL FIELD

The present invention relates to a method of manufacturing a hyaluronate-coated high-functional suture and a high-functional suture manufactured thereby, and more particularly to a method of manufacturing a high-functional suture and a high-functional suture manufactured thereby, in which a suture for internal and external surgery derived from a conventional chemical synthetic material is coated with a hyaluronate, which is a biocompatible material, to thus improve biocompatibility, functionality and ease of use.

BACKGROUND ART

A suture refers to a thread that is used to stitch a portion of a human body damaged by surgery or external injury. Since the beginning of use of sutures, widely employed has been catgut, which is made from intestinal extracts such as intestines, tendons, etc. of sheep, pigs or horses, but the use thereof is gradually decreasing because of incompatibility due to low strength, tissue rejection and fear of animal-derived diseases. Thereafter, alternative materials, such as nylon, silk, and the like, which are synthetic polymers having good properties, have been developed and widely utilized, but are disadvantageous because they have to be removed through additional surgery a predetermined period of time after being applied owing to the non-degradability and non-biocompatibility in the human body, and thus the use thereof is limited.

Accordingly, studies on the development and application of synthetic polymer sutures having ester bonds that are degraded upon prolonged exposure under water-soluble conditions have been continually conducted since the 1970s, and polyglycolic acid (PGA) was used early on, after which a polydioxanone (PDO) polymer or the like came to be widely used as a suture material.

Suture includes absorbable suture that is naturally absorbed in the body to thus obviate removal thereof after wound healing, and non-absorbable suture that requires removal after wound healing.

In the case of absorbable suture, degradable polymer materials such as PGA and PDO are mainly used for internal surgery, and in the case of non-absorbable suture, non-degradable polymer materials such as silk and nylon are mainly used for external surgery. Recently, the use of degradable suture that obviates post-treatment for removal after surgery is increasing. However, an absorbable suture having an ester bond composed of a chemical synthetic polymer causes a fear of side effects due to a foreign rejection reaction at the beginning of use, and degraded residue is present for a long period of time in the body even if degraded by body fluids in the body over time, and thus increasing biocompatibility and safety is regarded as more important.

These days, the use of such degradable sutures as beauty-related materials, such as lifting sutures for counteracting wrinkling, rather than for the original use thereof as a tissue repair material for tissue bonding after internal and external surgery, has greatly increased. The price of typical biodegradable suture amounts to 6~10 million won per kg, but the price of biodegradable suture made of the same material reaches at least 100 million won per kg upon lifting use, and thus the added value thereof is high, and interest in the development and application thereof is increasing.

Hyaluronic acid (HA) is a kind of glycosaminoglycan (GAG), which is an intermediate between chondroitin and heparin, and is a biopolymer widely present in the skin, muscles, cartilage, blood vessels, etc. in the human body. HA is an important ingredient for cell proliferation and activation in the human body, and it is known as a key element of anti-aging because the amount thereof is reduced in the body with aging to thus promote aging. Recently, the effect of HA on skin regeneration and anti-wrinkling through moisturizing and maintenance of elasticity has been confirmed, and thus the demand for beauty-related cosmetic products, foods and medical filler products is drastically increasing.

Generally, for ideal wound healing of a wound site, after intervention for the prevention of external contamination, cell proliferation and regeneration of the wound site, deposition of the substrate, and then closure of the wound quickly occur, and thus the wound is healed without adhesion or scarring. Methods of promoting such wound healing include, first, injecting a matrix serving as a substrate for wound healing, second, directly administering a growth factor capable of facilitating the expression of skin regenerative cells or therapeutic cells at a high concentration, third, administering an anti-inflammatory substance to suppress inflammation, and fourth, administering an anti-infection antimicrobial substance. Here, when only an in-vivo matrix such as HA is injected as a tissue repair material, the effect as a substrate in the human body may be expected, but in the case of direct administration of the growth factor, the growth factor is expensive, thus imposing price burdens and a difficulty in controlling the activity thereof upon administration. Furthermore, the addition of anti-inflammatory and antimicrobial substances is required for safety.

Thus, addition of the matrix such as HA with chitosan, chitin or lysine having anti-inflammatory and antimicrobial properties and with a compound such as triclosan is regarded as very effective, but a thorough review of the safety and properties thereof is required.

When a PDO suture, which is currently widely useful as a degradable suture using a synthetic polymer, is used as a material for internal surgery or as a material for external surgery such as skin junction in the human body, there is a concern about deterioration of the properties thereof due to low stability for body fluids compared to conventional non-degradable materials, and the use thereof is limited. Also, when it is used for the skin of the face as a suture for internal surgery or lifting, there is a concern about side effects such as a tissue rejection reaction due to an initial in-vivo foreign reaction and problems caused by absorption and discharge due to the degraded residue over the medium and long term after the injection. In particular, upon use as a lifting material for cosmetic surgery for a face, etc., side effects may occur, thus resulting in the deformation of outward appearances, rather than beauty improvement, which is the original goal of treatment. However, most studies for solving such problems have been merely limited to the production of degradable sutures by the addition of antimicrobial and anti-inflammatory ingredients or additives for improving mechanical properties, followed by melt spinning.

In the case of HA, many attempts have been made to manufacture a suture by adding HA to a degradable polymer suture material or to perform coating with HA during post-treatment after manufacture of the suture, in order to exhibit a skin filler function and various effects of improving elasticity and anti-wrinkling in the human body. However, upon the manufacture of a suture by adding a conventional suture material with a small amount of HA and then spinning it, the mechanical properties of the final suture may significantly deteriorate due to the insolubility of HA, and upon coating with HA during post-treatment after the manufacture of the suture, it is difficult to control the thickness of the suture due to high-viscosity HA, and the suture may be damaged by water in the HA aqueous solution used in the coating process, thus causing a concern of drastic deterioration of mechanical properties, and thus, there are no clear results.

Japanese Patent Application Publication No. 2011-31034 discloses a coated suture containing hyaluronic acid and a blend of a polymer derived from a vinyl lactam polymer with a polymer derived from a lactone polymer, but suffers from deteriorated mechanical properties as mentioned above.

Therefore, the present inventors have made efforts to solve the above problems and thus have ascertained that, when a suture is coated with a hyaluronate organic-solvent aqueous solution obtained by dissolving a hyaluronate in purified water and then adding an organic solvent thereto, a high-functional suture, in which the outer appearance and mechanical properties of the suture are maintained and biocompatibility and various physiological activities in the human body may be enhanced, may be manufactured, thus culminating in the present invention.

DISCLOSURE

Technical Problem

Accordingly, the present invention is intended to provide a suture and a method of manufacturing the same, in which the suture may exhibit superior biocompatibility, cushioning in the skin, and skin regeneration ability.

In addition, the present invention is intended to provide a filler for cosmetic surgery, a lifting thread, and a tissue-engineering scaffold, which may exhibit superior biocompatibility, cushioning in the skin, and skin regeneration ability.

Technical Solution

Therefore, the present invention provides a method of manufacturing a hyaluronate-coated suture, comprising the steps of: (a) preparing a hyaluronate organic-solvent aqueous solution having an organic solvent concentration of 50~70 vol % and a hyaluronate concentration of 0.5~2 vol % by dissolving a hyaluronate in purified water and then adding an organic solvent thereto; and (b) coating a suture with the hyaluronate organic-solvent aqueous solution and then drying the suture.

In the present invention, the hyaluronate of the hyaluronate organic-solvent aqueous solution has a weight average molecular weight of 5~100 kDa.

In the present invention, the suture is an absorbable suture or a non-absorbable suture.

In the present invention, the coating is performed by immersing the suture in the hyaluronate organic-solvent aqueous solution or spraying the hyaluronate organic-solvent aqueous solution onto the suture.

In addition, the present invention provides a hyaluronate-coated suture, manufactured by the above method.

In addition, the present invention provides a filler for cosmetic surgery, a lifting thread, and a tissue-engineering scaffold, comprising the above hyaluronate-coated suture.

Advantageous Effects

According to the present invention, a hyaluronate-coated suture is composed mainly of a chemical synthetic polymer, but the surface thereof is coated with hyaluronate, thus exhibiting outstanding safety and biocompatibility, and can be swollen and absorbed immediately after application into human bodies because of superior water absorbability, to thus minimize the pain of a patient and serve as formulations in various forms for tissue restoration.

BEST MODE

Figure 1:
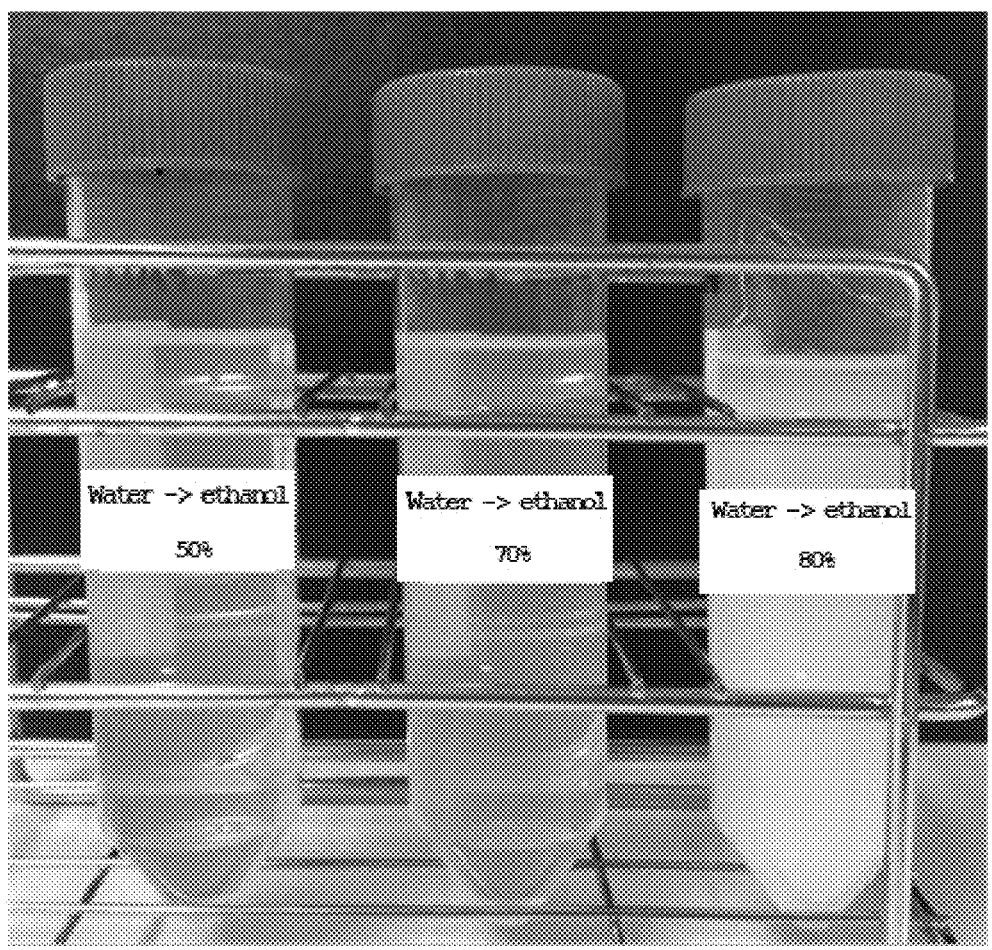
FIG. 1 shows the solubility of sodium hyaluronate organic-solvent aqueous solutions prepared by dissolving sodium hyaluronate in purified water and then adding an organic solvent thereto according to the present invention, depending on the concentration of the organic solvent.

Hyaluronate has very high hydrophilicity, and a degradable suture is gradually dissolved when exposed to water. Thus, in order to coat the suture with hyaluronate, the development of a solvent that dissolves hyaluronate but does not dissolve the suture is regarded as important.

In the present invention, when low-molecular-weight hyaluronate is dissolved in purified water and then an organic solvent is added thereto, a hyaluronate organic-solvent aqueous solution, in which the concentration of the organic solvent, which dissolves hyaluronate and does not damage the surface of the suture, is 50~70 vol % and the hyaluronate concentration is 0.5~2 vol % and, may be prepared, and easy coating of the suture using the hyaluronate organic-solvent aqueous solution is confirmed.

In an embodiment of the present invention, sodium hyaluronate having a weight average molecular weight of 10 kDa is dissolved in purified water and ethanol is added thereto, thereby preparing a sodium hyaluronate ethanol aqueous solution, in which the ethanol concentration is 50~70 vol % and the sodium hyaluronate concentration is 0.5~2 vol %, after which a PDO suture is immersed in the sodium hyaluronate ethanol aqueous solution so that the surface of the PDO suture is coated with sodium hyaluronate. The surface of the PDO suture coated with sodium hyaluronate was observed using a microscope, from which smooth coating was confirmed to result without surface damage.

An aspect of the present invention addresses a method of manufacturing a hyaluronate-coated suture, comprising the steps of (a) preparing a hyaluronate organic-solvent aqueous solution having an organic solvent concentration of 50~70 vol % and a hyaluronate concentration of 0.5~2 vol % by dissolving a hyaluronate in purified water and then adding an organic solvent thereto; and (b) coating a suture with the hyaluronate organic-solvent aqueous solution and then drying the suture.

In the present invention, the hyaluronate is configured such that hyaluronic acid is coupled with a salt, and examples thereof may include, but are not limited to, sodium hyaluronate, potassium hyaluronate, calcium hyaluronate, etc.

The hyaluronate has a weight average molecular weight of 5~100 kDa, and preferably 10~20 kDa. If the molecular weight of the hyaluronate exceeds 100 kDa, a solution obtained by dissolving the hyaluronate at a concentration of 0.5~2% in a 50~70% organic-solvent aqueous solution may become viscous due to the high molecular weight of the hyaluronate, making it difficult to adjust the thickness of the suture upon conventional suture coating through immersion or spraying and also to achieve dissolution even in a 50% organic-solvent aqueous solution. The viscosity of the hyaluronate is preferably set to the range of 20 cps or less based on a 1% solution.

When hyaluronate is dissolved in purified water, heating may be performed in order to reduce the molecular weight of hyaluronate and to efficiently achieve dissolution. Here, heating is preferably conducted at 40~70° C. When hyaluronate is dissolved, an organic solvent is added, thus preparing a hyaluronate organic-solvent aqueous solution having an organic solvent concentration of 50~70 vol % and a hyaluronate concentration of 0.5~2 vol %.

If the concentration of the organic solvent is less than 50 vol %, the surface of the suture may be damaged during the coating process. On the other hand, if the concentration of the organic solvent exceeds 70 vol %, hyaluronate may be deposited, and thus the coating process cannot be performed.

As the organic solvent, any organic solvent may be used without limitation, so long as it dissolves hyaluronate but does not dissolve the suture, and examples thereof may include ethanol, acetone, etc.

After the dissolution of the hyaluronate in purified water, in the case where the organic solvent is not added but hyaluronate is directly dissolved in a 50~70% organic-solvent aqueous solution, hyaluronate may not be dissolved, or dissolution thereof to the high concentration may be impossible, and thus the suture coating process cannot be conducted.

In the present invention, the suture may include a typically useful absorbable suture or non-absorbable suture.

Examples of natural material-based absorbable suture may include catgut and chromic gut, and examples of synthetic material-based absorbable suture may include polyglycolic acid (Dexon, Mexon), polyglactin 910 (Vicryl) and polydioxanone. Also, an example of natural material-based non-absorbable suture may include silk, and examples of synthetic material-based non-absorbable suture may include polyester (Dacron), polypropylene (Proline), polyamide (Nylon) and e-PTFE (Gore-Tex), but the present invention is not limited thereto.

The step of coating the suture with the hyaluronate organic-solvent aqueous solution may be performed by immersing the suture in the hyaluronate organic-solvent aqueous solution or spraying the hyaluronate organic-solvent aqueous solution onto the suture.

According to the present invention, the suture may be coated with hyaluronate alone, but carrier or excipient components, which are typically used in the art, may be further added depending on the field of use thereof, and the kinds and amounts thereof are not particularly limited.

In order to ensure more enhanced functionality upon application for sutures for internal and external surgery and beauty-related lifting, which are the main end use of the present invention, a pharmacologically acceptable biocompatible agent, such as chitosan, polylactic acid, and other anti-inflammatory materials, may be used in combination.

Another aspect of the present invention addresses a hyaluronate-coated suture manufactured by the above method.

The hyaluronate-coated suture according to the present invention, the surface of which is coated with hyaluronate, may exhibit outstanding safety and biocompatibility, and may be swollen and absorbed immediately after application into the human body because of superior water absorbability, to thus minimize the pain of a patient, and may be utilized as formulations in various forms for tissue restoration. Furthermore, when a 50~70% ethanol aqueous solution is used as the solvent, microbial contamination of existing sutures may be minimized.

Thus, a further aspect of the present invention addresses a filler for cosmetic surgery, a lifting thread, and a tissue-engineering scaffold comprising the aforementioned hyaluronate-coated suture.

MODE FOR INVENTION

A better understanding of the present invention may be obtained through the following examples, which are set forth to illustrate, but are not to be construed as limiting the scope of the present invention, as will be apparent to those skilled in the art.

Example 1: Preparation of Low-Molecular-Weight Sodium Hyaluronate Aqueous Solution A sodium hyaluronate aqueous solution having a molecular weight of 50 kDa was prepared by dissolving sodium hyaluronate (Hi-Aqua™, made by JinWOO Bio) having a molecular weight of 0.3 MDa at a concentration of 1~5% in purified water and then performing thermal treatment at 70° C. for 1 hr.

Comparative Example 1: Preparation of Low-Molecular-Weight Sodium Hyaluronate Aqueous Solution A sodium hyaluronate aqueous solution was prepared by dissolving sodium hyaluronate (Hi-Aqua™, made by Jin-WOO Bio) having a molecular weight of 0.3 MDa at a concentration of 1~5% in purified water.

Example 2: Preparation of Low-Molecular-Weight Sodium Hyaluronate Aqueous Solution A sodium hyaluronate aqueous solution was prepared by dissolving sodium hyaluronate (Hi-Aqua™, made by Jin-WOO Bio) having a molecular weight of 10 kDa at a concentration of 1~5% in purified water.

Examples 3 to 5: Preparation of
Low-Molecular-Weight 0.5~2% Sodium
Hyaluronate Ethanol Aqueous Solutions Sodium hyaluronate ethanol aqueous solutions (ethanol concentration: 50~70%; sodium hyaluronate concentration: 0.5~2%) were made by adding ethanol to the respective sodium hyaluronate aqueous solutions of Examples 1 and 2 and Comparative Example 1.

Comparative Example 2: Preparation of
Low-Molecular-Weight 0.5~2% Sodium
Hyaluronate Ethanol Aqueous Solution 0.5~2% sodium hyaluronate ethanol aqueous solutions were prepared by dissolving sodium hyaluronate (Hi-Aqua™, made by JinWOO Bio), having a molecular weight of 10 kDa, in 50~70% ethanol aqueous solutions, unlike Examples 1 to 3 and Comparative Example 1.

Test Example 1: Measurement of Solubility of
Low-Molecular-Weight Sodium Hyaluronate in
Purified Water and in Ethanol Aqueous Solution at
Different Concentrations The solubility of the sodium hyaluronate aqueous solutions of Examples 1 and 2 and Comparative Example 1 and the sodium hyaluronate ethanol aqueous solutions of Example 3 and Comparative Example 2 was observed with the naked eye.

As shown in FIG. 1, efficient dissolution occurred in all of the sodium hyaluronate ethanol aqueous solutions (Example 4) having ethanol concentrations of 50~70% obtained by adding ethanol to the sodium hyaluronate (M.W. 10 kDa) aqueous solution (Example 2).

Figure 2:
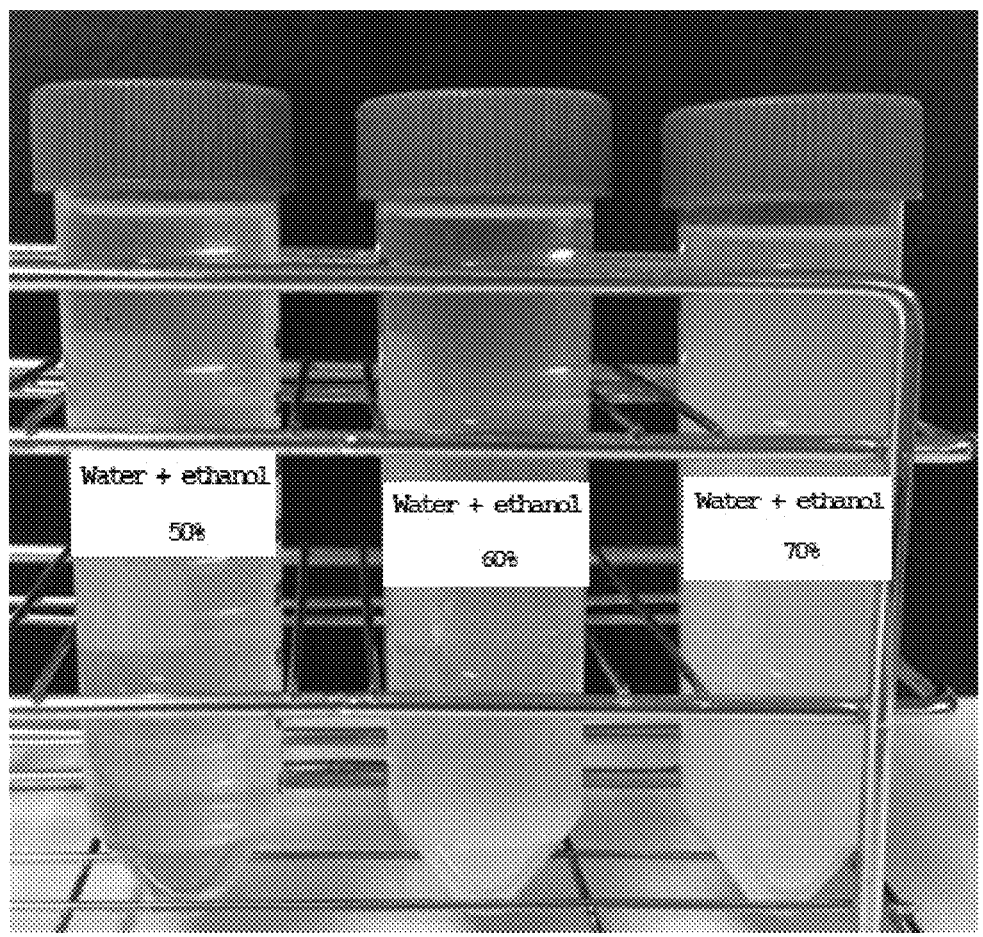
FIG. 2 shows the solubility of sodium hyaluronate organic-solvent aqueous solutions prepared by dissolving sodium hyaluronate in an organic solvent aqueous solution, depending on the concentration of the organic solvent.

In contrast, as shown in FIG. 2, in Comparative Example 2, in which sodium hyaluronate (M.W. 10 kDa) was directly dissolved in 50~70% ethanol aqueous solutions, sodium hyaluronate was dissolved in a 50% ethanol aqueous solution but was not completely dissolved in a 60% ethanol aqueous solution.

Also, in the sodium hyaluronate ethanol aqueous solutions (Example 3) having ethanol concentrations of 50~70% obtained by adding ethanol to the sodium hyaluronate (M.W. 50 kDa) aqueous solution (Example 1) resulting from dissolving sodium hyaluronate (M.W. 0.3 MDa) at a concentration of 1~5% in purified water and then performing thermal treatment, sodium hyaluronate was dissolved at ethanol concentrations up to 60%, but was deposited in the form of crystals at ethanol concentrations exceeding 60%, and thus incomplete dissolution thereof was confirmed.

In the sodium hyaluronate ethanol aqueous solutions (Example 5) having ethanol concentrations of 50~70% obtained by adding ethanol to the sodium hyaluronate (M.W. 0.3 MDa) aqueous solution (Comparative Example 1), sodium hyaluronate was dissolved at ethanol concentrations up to 50%, but was deposited in the form of crystals at ethanol concentrations exceeding 50%, and thus incomplete dissolution thereof was confirmed.

Test Example 2: Measurement of Stability of PDO
Suture in Purified Water and in Ethanol Aqueous
Solution at Different Concentrations A PDO suture (Meta Biomed) was immersed in purified water and 50, 60, 70, 95% ethanol aqueous solutions, after which changes in the surface of the suture were observed using an electron microscope. The results are shown in FIGS. 3 to 5.

Figure 3:
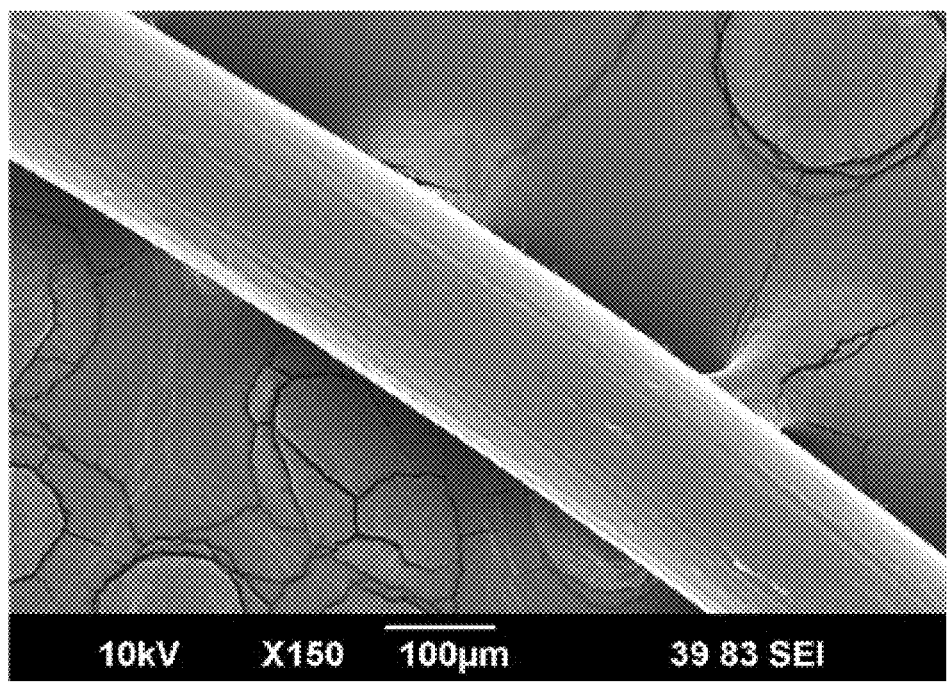
FIG. 3 shows an electron microscope image of the surface of a non-coated PDO suture.
Figure 4:
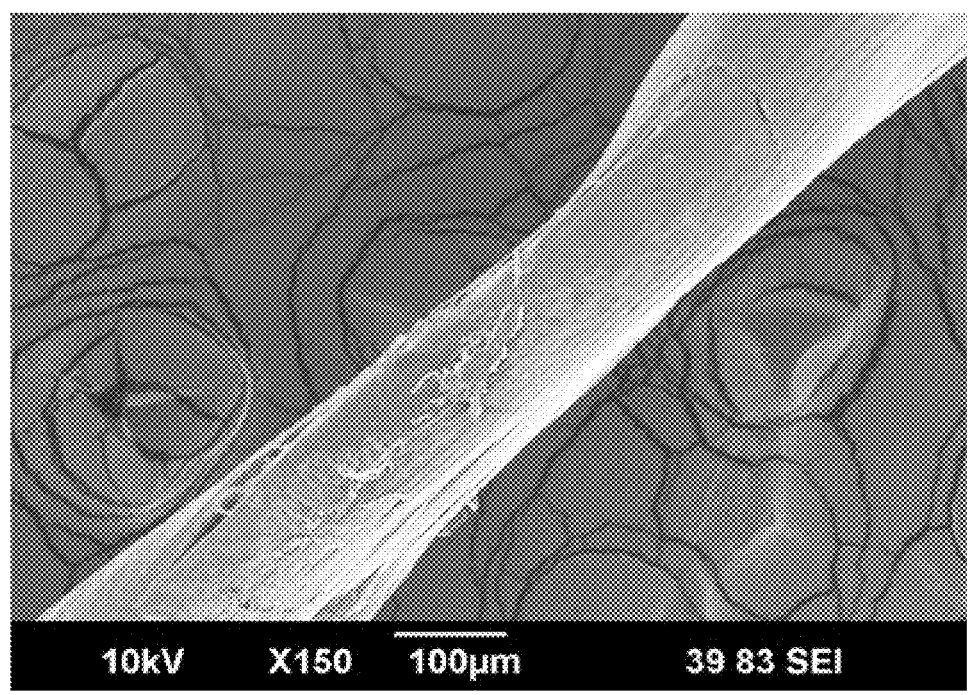
FIG. 4 shows an electron microscope image of the surface of a PDO suture immersed in purified water.

As shown in FIGS. 3 and 4, the surface of the PDO suture not subjected to coating treatment was smooth, and the surface of the PDO suture immersed in purified water was dissolved and thus considerably damaged. In the 50%~60% ethanol aqueous solutions, a portion of the surface of the PDO suture was damaged but the PDO suture was able to serve as a suture, and in the 70% ethanol aqueous solution, surface damage was not observed.

Figure 5:
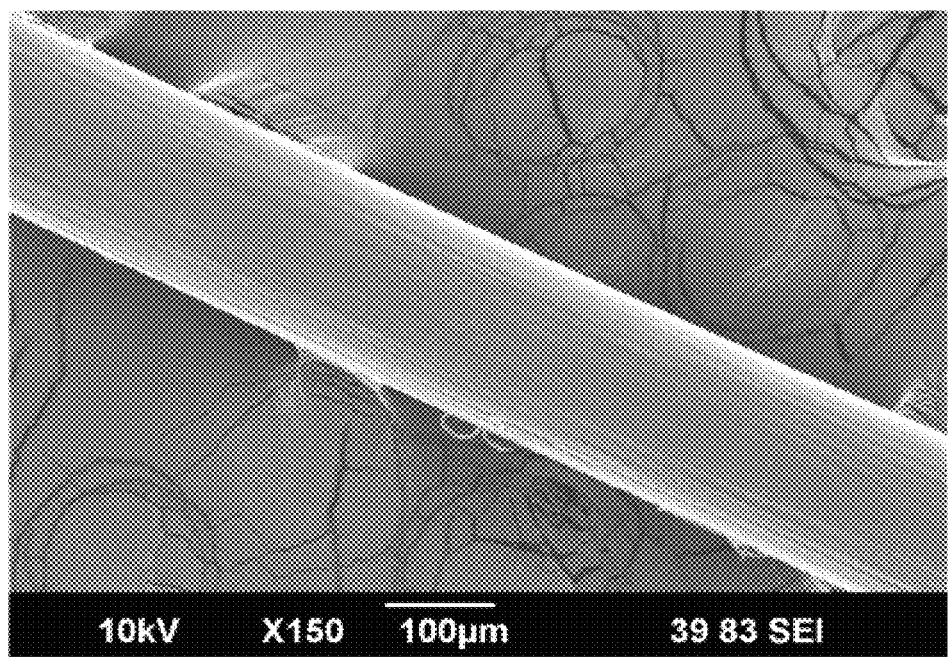
FIG. 5 shows an electron microscope image of the surface of a PDO suture immersed in a 95% organic solvent.

As shown in FIG. 5, the surface of the PDO suture immersed in 95% ethanol was very similar to the intact surface of a PDO suture.

Based on the aforementioned results, the use of the sodium hyaluronate aqueous solution obtained by dissolving sodium hyaluronate in purified water in order to coat the PDO suture with sodium hyaluronate was found to cause damage to the surface of the PDO suture, making it impossible to realize effective coating.

Example 6: Coating of Suture with Sodium
Hyaluronate Through Immersion

A PDO suture was coated with sodium hyaluronate through immersion for 1 min in the sodium hyaluronate ethanol aqueous solution (ethanol concentration: 70%; sodium hyaluronate concentration: 1%) of Example 4.

Test Example 3: Evaluation of Surface Change of
PDO Suture Coated with Sodium Hyaluronate in
70% Ethanol Aqueous Solution Changes in the surface of the PDO suture coated with sodium hyaluronate of Example 6 were observed using an electron microscope. The results are shown in FIG. 6.

Figure 6:
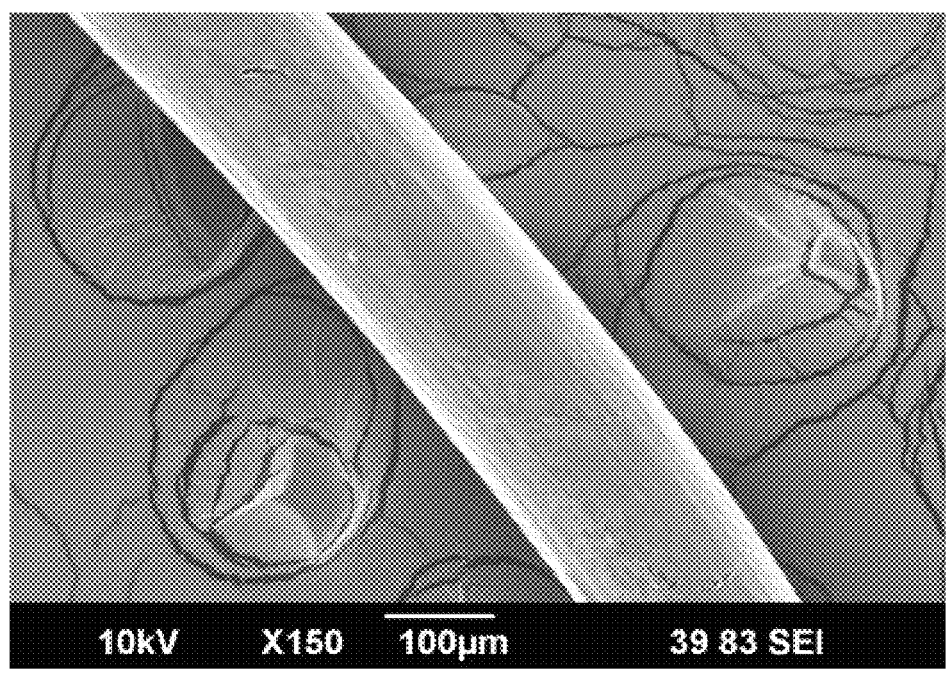
FIG. 6 shows an electron microscope image of the surface of a PDO suture coated with a sodium hyaluronate organic-solvent aqueous solution (ethanol concentration: 70%; sodium hyaluronate concentration: 1%) prepared by dissolving sodium hyaluronate in purified water and then adding an organic solvent thereto according to the present invention.

As shown in FIG. 6, the 70% ethanol aqueous solution was seen to implement coating with sodium hyaluronate in the form of a partial spherical shape or a slight protrusion on the surface of the PDO suture, without damage to the surface of the PDO suture.

Although specific embodiments of the present invention have been disclosed in detail as described above, it is obvious to those skilled in the art that such description is merely of preferable exemplary embodiments and is not construed to limit the scope of the present invention. Therefore, the substantial scope of the present invention will be defined by the appended claims and equivalents thereof.

INDUSTRIAL APPLICABILITY

The hyaluronate-coated suture of the present invention can be utilized for a filler for cosmetic surgery, a lifting thread, a tissue-engineering scaffold, etc.

The invention claimed is:
1. A method of manufacturing a hyaluronate-coated suture, comprising the steps of:
(a) preparing a hyaluronate organic-solvent aqueous solution having an organic solvent concentration of 50~70 vol % and a hyaluronate concentration of 0.5~2 vol % by dissolving a hyaluronate in purified water and then adding an organic solvent thereto; and
(b) coating a suture with the hyaluronate organic-solvent aqueous solution and then drying the suture.
2. The method of claim 1, wherein the hyaluronate of the hyaluronate organic-solvent aqueous solution has a weight average molecular weight of 5~100 kDa.

3. The method of claim 1, wherein the coating is performed by immersing the suture in the hyaluronate organic-solvent aqueous solution or spraying the hyaluronate organic-solvent aqueous solution onto the suture.

* * * * *